United States Patent [19]

Fuchs

[11] Patent Number: 5,042,097
[45] Date of Patent: Aug. 27, 1991

[54] BED FOR SNORERS

[76] Inventor: Sieglinda Fuchs, Auf der Hofreith, D-4000 Duesseldorf, Fed. Rep. of Germany

[21] Appl. No.: 487,970
[22] PCT Filed: Jul. 19, 1989
[86] PCT No.: PCT/EP89/00845
    § 371 Date: Jun. 1, 1990
    § 102(e) Date: Jun. 1, 1990
[87] PCT Pub. No.: WO90/01912
    PCT Pub. Date: Mar. 8, 1990

[30] Foreign Application Priority Data

Aug. 17, 1988 [DE] Fed. Rep. of Germany ....... 3827878
Sep. 17, 1988 [DE] Fed. Rep. of Germany ....... 3831699
Oct. 25, 1988 [DE] Fed. Rep. of Germany ....... 3836292

[51] Int. Cl.⁵ .............................................. A61G 7/04
[52] U.S. Cl. .............................................. 5/61; 5/109; 128/33
[58] Field of Search ............ 5/61, 108, 109, 184, 5/185, 200 B, 201, 202; 128/33

[56] References Cited

U.S. PATENT DOCUMENTS

| 2,433,548 | 12/1947 | Ecks | 128/33 |
| 3,056,145 | 10/1962 | McKinley et al. | 5/109 |
| 3,590,812 | 7/1971 | Larson | 128/33 |
| 3,748,666 | 7/1973 | Seng | 5/61 |
| 4,114,209 | 9/1978 | Sandlin | 5/108 X |
| 4,175,550 | 11/1979 | Leininger et al. | 5/109 X |
| 4,654,903 | 4/1987 | Chubb et al. | 5/108 |

FOREIGN PATENT DOCUMENTS

| 210469 | 4/1956 | Australia | 5/61 |
| 1021502 | 11/1977 | Canada | 5/108 |
| 560715 | 10/1932 | Fed. Rep. of Germany. | |
| 1837239 | 9/1961 | Fed. Rep. of Germany. | |
| 1151347 | 7/1963 | Fed. Rep. of Germany. | |
| 1198005 | 4/1966 | Fed. Rep. of Germany. | |
| 2408784 | 8/1975 | Fed. Rep. of Germany. | |
| 2636746 | 7/1979 | Fed. Rep. of Germany. | |
| WO86/03663 | 7/1986 | PCT Int'l Appl. . | |

Primary Examiner—Michael F. Trettel
Attorney, Agent, or Firm—Spencer & Frank

[57] ABSTRACT

A bed for preventing snoring includes a support; a mattress base tiltably secured to the support so as to provide for tilting motions of the mattress base about a longitudinal pivotal axis thereof; a drive for imparting a tilting motion to the mattress base out of and into a horizontal position; a load-sensitive switch operatively connected with the mattress base and the drive for tilting the mattress base out of the horizontal position in a direction opposite to a torque imparted by a load to the mattress base and limit switches operatively connected to the drive and cooperating with the mattress base for deenergizing the drive when the mattress base attains a predetermined tilted position during tilting motion from the horizontal position or when the mattress base attains the horizontal position during tilting motion from a tilted position.

13 Claims, 5 Drawing Sheets

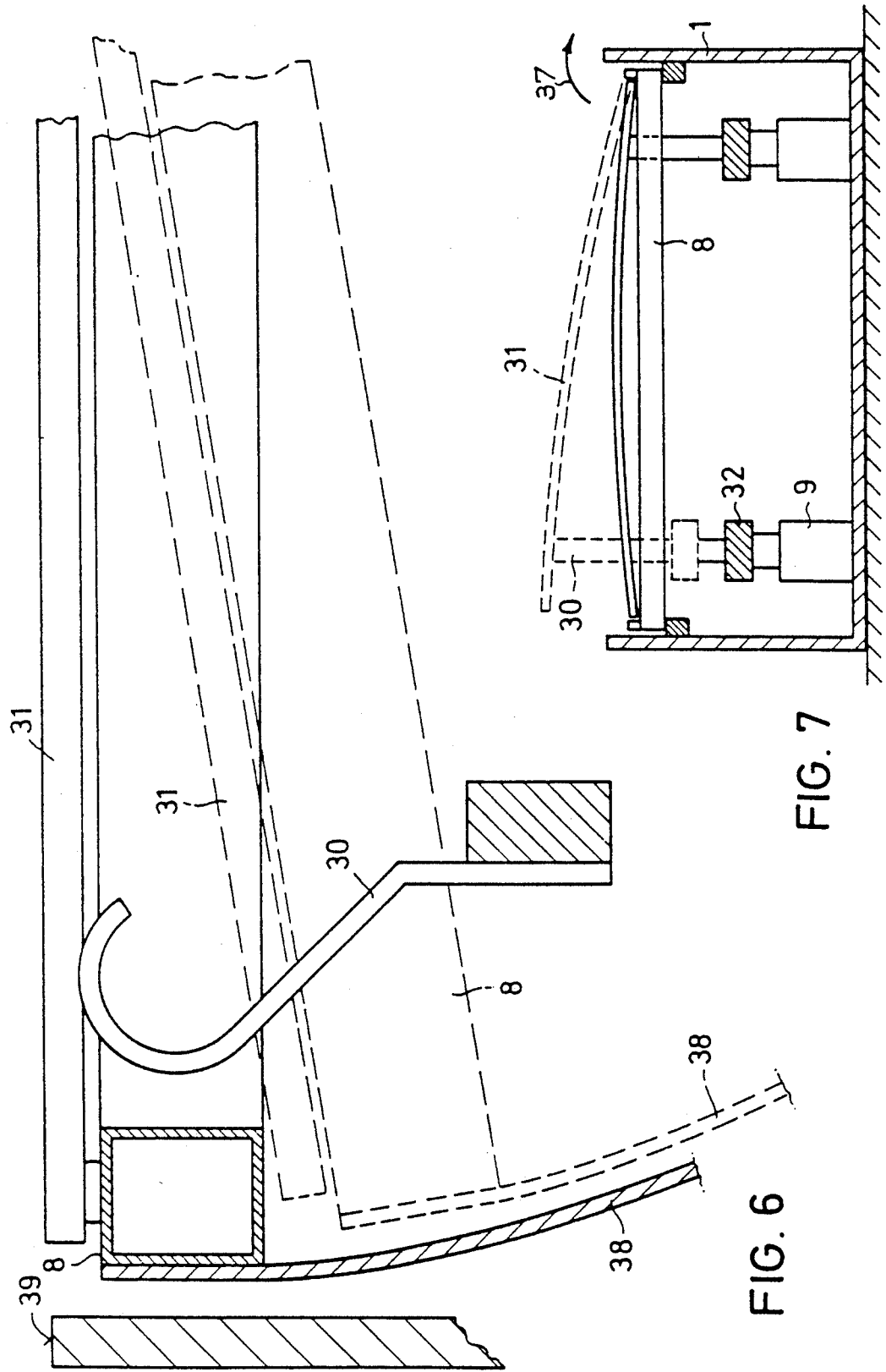

BED FOR SNORERS

BACKGROUND OF THE INVENTION

The invention relates to a bed having an influence on snoring, said bed having a mattress base, which is designed to be tiltable at least around a longitudinal axis. The mattress base has essentially plane resting surface and is joined to a preferably electro-motorized tilting drive which is connected by means of a control to a power supply.

In the past many attempts were made, in various ways, to prevent the snoring of sleeping people since the sound caused thereby significantly disturbs any person sleeping in the same room where from time to time snoring can become so loud that even the sleeping person himself wakes up. If one wakes up the snorer, snoring stops, but his sleep has been interrupted. However, after going back to sleep, snoring starts again, often shortly afterwards. In most cases it has been realised that the snoring sounds do not occur if and as long as the person concerned rests on a side position. In order to force such side position, a device is known from German Auslegeschrift (application published after examination) 11 98 005 which consists of a padded board having the same length as the upper part of the body and which is hinged along the longitudinal axis. The board is equipped with a locking device which can lock the part that can be lifted up at an angle of between 60° and 90°. The device is equipped at both ends with loops through which one leg and one arm are put through so that the sleeping person is forced into the side position by the part that is lifted up. Irrespective of the non-yielding body support, restful sleep is not possible with such a device since the sleeping person is pinned in a side position and is not able to turn around. Due to the arm loop, no free movement, not even e.g. the support of the head by an arm, is possible in the side position. Another disadvantage of the known device is that due to the loop placed around the thigh and the shoulder, blood circulation can be restricted.

From U.S. Pat. No. 3,089,130 a device for mounting on a bed is known in which the head of the sleeper is put on a head support which can be tilted and is equipped with a vibrator. Sounds of snoring are picked up by a microphone and are fed as a control signal to a control which then activates the vibrator. By means of the vibrator the head of the sleeping person is shaken up and down so that the latter wakes up and snoring ceases. Such a device does indeed stop the snoring very effectively, but, to a large extent, is unhealthy since the sleep of the snorer is interrupted over and over again. From German Auslegeschrift 11 51 347 a similar device is known which, however, causes the head of the sleeping person, resting on a horizontally movable support, to be moved back and forth. Switching on the device again takes place by means of a microphone. With this device, only the head is turned to the side, regardless of the position of rest of the body, by a horizontal conveyor belt which can be moved back and forth or by a horizontal board which can be slid back and forth so that because of the non-restricted forces, there is a risk of damage to the cervical vertebrae. The tilting of the head to the side, forced on by the device and which is especially unnatural for the sleeping position, inevitably has to lead to interruption of sleep so that, also here, in addition to the risk of damages to the cervical vertebrae, undisturbed sleep cannot be ensured either.

International Application WO 86/03663 describes a mattress which is longitudinally divided into three parts of which the middle one is supported on a tilting board by means of springs. In this case the supine position can only be assumed if the sleeper lies on the middle section exactly above the tilting roll. For each small move of the body sideways with respect to the tilting section support, the tilting board tilts to the side so that the middle section and the adjacent side section, also supported by springs, adopt in cross-section, a V-shaped orientation. If the sleeping person, while in the supine position lies approximately on the joint between the middle section and the side section of the mattress, then these two adjoining sections are buckled into a V-shape so that the mattress by and large has the effect of the infamous "dip" of an old worn mattress. If the snorer is first on his back in the V-shaped buckled joint area between the middle- and side section, then he has no possibility whatsoever to turn himself or be turned by a partner into the snore stopping side position since, due to the effect of the tilting board, the body always has to be moved "up hill". The same disadvantage is attached to the bed design which is known from German Patent 560 715 and which has a V-shaped foldable mattress support. From U.S. Pat. No. 3,013,281, German Utility Model 18 37 239, as well as German Offenlegungsschriften (application published without examination) 26 36 746 and 24 08 784 hospital beds are known which essentially have a trough-shaped resting surface and in which the mattresses or the mattress base can be tilted around the longitudinal axis. Such beds serve first to help the nursing personnel when transferring patients, but are also intended to vary the pressure on individual body parts where the body of the patients for medical reasons, e.g. in the case of fractures or the like, may not change position relative to the resting surface due to the tilting. In certain cases, the circulation in bedridden persons is supposed to be aided by rocking motions of the resting surface (German Utility Model 18 37 239 and German Offenlegungsschrift 24 08 784). None of these known beds are suitable for domestic use since in practice these are so-called trough beds which are supposed to secure the lying person in a given position while clearly an essential aspect of a bed for normal residential purposes is that, in use, an unrestricted freedom of movement is provided by a practically uniform resting surface.

This type of bed must also be available to the sleeping person so that the latter also during his sleep should be able to move unrestrictedly into another position, for example turning from the side on to the back and on to the other side.

In summary, it has been found that the devices developed specifically so far to prevent snoring, are unsuitable for daily use. Even if beds are known which are designed with at least parts of the mattress or the mattress base tiltable around the longitudinal axis, they are designed for hospital needs or the care of bedridden persons and are constructed in such a way that their use as normal beds for domestic requirements is not possible and besides, the free movement of a sleeping person in such beds is to a large extent restricted.

SUMMARY OF THE INVENTION

An object of the invention is to provide a bed of the type described above which prevents snoring or stops the snoring shortly after its starts without or with only the slightest restriction of the freedom of movement of the sleeping person. The construction has to be designed in such a way that the device can be used in a domestic setting and fulfills all domestic requirements.

According to the invention, the problem may be solved if the mattress base is preferably provided with non-contact limit switches which switch off the driving mechanism each time the sloping position or horizontal position is reached. Such a bed design has the advantage that the sleeping person can use the bed without any restriction on his freedom of movement and can lie as desired on the back and on either side. In the majority of cases people start to snore when deep sleep starts and if they are on their back. A person sleeping in the same room and who is disturbed by the snoring sound, can now start by means of a suitable switch, preferably a simple touch switch, the geared motor, something which also can be carried out when one is half asleep, so that at this point the mattress base together with the mattress and the sleeping person is tilted up in a set sloping position. Surprisingly, it has been found that with a sloping position of between 10° and 25° a sleeping person, lying on his back, within a short time rolls himself into the side position without waking. If the bed is kept for a period of a few minutes in this sloping position, the sleeping person moves by himself into a stable side position so that then the bed can be tilted back again by hand to the horizontal position. However, it is especially useful if the control is connected to a short-interval time switch which after a given time has lapsed, switches on the tilting drive to return the bed to the horizontal position. In this way the bed returns to its normal position without the sleeping person immediately turning again on his back. On the other hand, the sleeping person lying there, is not prevented from moving freely and can even move, after some time, into another sleeping position. Often, when sleeping on one side for some. time, the other side is taken so that in spite of the horizontal position of the resting surface, the sleeping person in question does not immediately start snoring again.

On the other hand, the person who initiates the tilting movement does not have to take care that the bed, after the snoring has ceased, returns to the normal position. Rather this takes place automatically. The use of an electric motor, preferably an electric geared motor, has the advantage that the tilting movement can be carried out practically without any disturbing running noise using small motors of low electrical power. The tilting axis of the mattress base can in its simplest form be arranged on a long side, so that the mattress base with the other long side edge, depending on the available height above the floor, can be brought out of the horizontal position into the sloping position by tilting down or tilting up.

According to an advantageous embodiment of the invention, for a bed with a mattress base which can be tilted around at least one longitudinal axis, preferably around the longitudinal central axis, in both directions from the horizontal position, a load sensitive switch is further provided which controls the direction of each of the tilting movements from the horizontal position to oppose the load moment given by a onesided load on the mattress base. Since the sleeping person does not always lie in the supine position exactly in the longitudinal central axis of the mattress base or the mattress, but can also likely lie only on one of the sides of the mattress, this embodiment has the advantage that for the sloping position, the mattress base is tilted up on the side on which the sleeping person in question lies so that there is adequate room for movement to lie on the side. Depending on the design of the tilting drive, the load sensitive switch should be installed on the box frame of the bed between the mattress base and the support of the tilting drive, e.g. where the motor is attached to the bed box frame since in this place the load moment can be detected as tensile- or compressive force. Switching can also be carried out by determining the load on the motor. The mattress base can be carried either on the two long sides so that it can be tilted to one or the other side as the case may be, or is supported so it can be tilted to both sides around the longitudinal central axis.

The mattress base can be supported at the end using either a shaft journal on the bed box frame or a separate supporting frame. The drive motor can transfer the torque directly via a shaft journal in which case an appropriate gearing has to be provided. The tilting around a longitudinal axis can also be accomplished by connecting the mattress base in each case at the end to the bed frame or its supporting frame by means of two tilting levers where the two tilting levers may not be parallel but have to be at an angle to one another in the tilting plane. The base of the mattress can be connected by "suspended"from the tilting levers but can also be connected by "stand" thereon. This design forms at both ends a so-called four-bar-chain and an adjustment of the angles formed between the levers, their length and the distance between the bar and the mattress base or the box frame of the bed can influence the tilting angle and its dependence on the driving stroke, e.g. a connecting rod.

Instead of a single rigid mattress base, the latter can also be divided lengthwise so that corresponding to the control of the motor by the load dependent switch one longitudinal half or the other longitudinal half is tilted up and is tilted back after an appropriate time.

According to an embodiment of the invention, an electric geared motor, which acts on a connecting rod, constitutes the tilting drive. With such a tilting drive the required torques for the tilting can also be generated with small electric motors in which case the tilting is completed in a relatively short time so that the sleeping person, as desired, immediately moves on to his side. The connecting rod can be designed as a rack or a screw spindle. A screw spindle drive has the advantage of running quieter and having greater gear ratio so that even with small motors, high torques can be exerted by means of the connecting rod.

According to another embodiment of the invention, the geared motor is installed at the end under the mattress base and at a distance from the tilting axis. This arrangement has the advantage that the standard overall length of a bed is not exceeded since the already available free space under the mattress base is used for the installation of the geared motor. Through an appropriate selection of the distance between the geared motor and the tilting axis, the torque to be applied here can be considerably reduced. The motor should be installed as far as possible from the tilting axis.

According to a preferred embodiment of the invention, in particular for a mattress base which can be tilted around the longitudinal cehtral axis, the connecting rod is connected with the load sensitive switch of the control giving the direction of the load moment. In this embodiment, one relies on the fact that with regard to the cross direction, the centrally supported mattress base acts as a balance beam so that the tilting drive "feels" on which half of the mattress the sleeping person lies. If the snoring starts, the tilting drive is switched on to turn in such a way that the loaded mattress half is tilted up so that again it is ensured that the sleeping person turns on his side towards the empty half of the bed. This effect can also be used if the mattress base in each case is provided with tilting bearings on the long sides and each long side is connected with a lifting drive. To tilt, the drive is then actuated on the side on which the highest load moment acts.

According to a specially advantageous embodiment of the invention, an electro-acoustic sensor is provided which is connected to the control and which in the case of sounds of snoring switches on the tilting drive. In active areas, this electro-acoustic sensor can consist of a simple microphone which is provided with an appropriate control that switches on the tilting drive when a certain sound level is exceeded.

However, the electro-acoustic sensor control can also be designed in such a way that the tilting drive is only switched on if sounds of a given sound level and within a certain frequency range, namely the low frequency range usual for snoring, are detected over a certain period. This arrangement has the advantage that the tilting drive is switched on as a result of the sounds produced by snoring. In this way a person, sleeping in the same room, does not have to actuate a switch. The particular advantage is that also for a snorer sleeping by himself, the snoring ceases within a short time. The reason that this is important is because according to recent medical investigations, snoring is also detrimental to the health of the snorer himself.

A preferred embodiment provides that fixed holding elements are attached to both long sides of the mattress base for the edge of the mattress. This arrangment has the advantage that without additional movable parts on the side which tilts down in each case, the mattress is kept in its original position at the edge by means of the holding elements and thus a somewhat horizontal resting surface to support the body in the side position continues to exist. The flexibility of a modern mattress is sufficient to form a smooth transition from the sloping surface to the essentially horizontal edge surface. According to the invention the holding elements are attached in a comblike fashion along both long sides to the fixed parts of the bed.

A particular embodiment of the invention provides that the mattress base is formed as a platform of slats, known per se, the slats being spaced at right angles to the longitudinal axis. Holding elements are attached to the bed at the long sides of the mattress base and in each case protrude from below into the gap between two slats. Their top ends are essentially in the plane of the platform of slats when the mattress base is in the horizontal position. This embodiment can also be modified so that the slat platform itself remains in its original position and only the mattress is lifted from the edge by means of appropriately designed holding elements, connected to a drive, and is brought into the required sloping position over a sufficient width so that the body of the sleeping person can roll into the side position. Load sensitive sensors may also be provided in this case for the respective drives so that the mattress is lifted on the "right" side when sounds of snoring occur. This arrangement can be made in such a way that the holding elements via their drive are supported directly on the floor of the room or on the bottom of the box frame of the bed so that through appropriate change in height, one mattress side is tilted up. In a variant of this design it is also possible within the framework of the invention to support the mattress base itself using at least two legs which can be adjusted in height by means of a drive and by means of which the tilting then can be achieved. By installing four legs whose height can be adjusted, where the legs installed on one long side can in each case be operated synchronously, a special tilting support can be omitted for the mattress base depending on the design.

According to another embodiment of the invention, the mattress base at the edge of the part which protrudes from the horizontal plane during tilting, may have a downwardly directed protective skirt extending into the bed box frame. Such a protective skirt installed at least along the long sides, ensures that in the tilted up position nothing can get into the gap opening up between the mattress base and the edge of the bed box frame so that injuries are avoided when turning around.

According to the invention, for a bed of the type described above, a conversion set is proposed which is characterized by two end parts which each have a tilting bearing for the mattress base and which are equipped with height-adjustable legs. While in the manufacture of beds, the tilting bearing for the mattress base as well as the attachment of the tilting drive do not pose any problem, the later conversion of existing beds causes considerable problems. To start with, the dimensions of mattresses are not standardized with the dimensions of beds, so that different heights have to be taken into consideration. Furthermore, it must be taken into consideration that with the materials used or because of the design, e.g. for veneered or fabric covered bed box frames, the later conversion to install the tilting bearing is not possible since the total weight of the sleeping person now has to be carried by both end mounted tilting bearings instead of by the long ledges on the bed box frame. For this, the dimensions and also the strengths of materials used in the construction of the box frame of the bed are usually not adequate. The embodiment according to the invention, now makes it possible to install in an existing bed box frame, in the form of a conversion set, both end parts which are equipped with the tilting bearings and support the mattress base. By appropriate adjustment of the height of the legs, the supporting surfaces of the mattress base, taking into consideration the thickness of the existing mattress, can be adjusted exactly to the height of the existing bed box frame. With a centrally supported mattress base the latter is narrower than the original mattress base so that the base of the mattress can freely extend past the supporting ledges of the box frame of the bed. The height adjustment has to be carried out in such a way that the tilting operation together with the carried mattress can take place practically unhindered within the angle given by the tilting.

The end parts, provided with legs, can then be fixed to the appropriate ends of the bed box frame, e.g. by means of screws, in order to ensure a perfect support and alignment of the end parts. However, in many cases, since the materials of the existing bed box frame are not suitable for using screws capable of carrying heavy loads, an advantageous embodiment of the invention provides that both end parts are securely connected to one another via at least a longitudinal bar. In this way a self-supporting insert piece is obtained which is independent of the box frame of the bed. Especially for mattress bases, of which the tilting axis is in the longitudinal central axis, it would be useful if the longitudinal bar be connected with the end part below the tilting bearing.

In this way it is ensured that the mattress base can freely be tilted to both sides. In order to be able to fit such a conversion set on an existing bed box frame, further provision has been made so that the longitudinal bar be designed in such a way that its length is adjustable. This can be obtained e.g. by means of a segmented longitudinal bar which is designed to overlap at the joint and which is provided with a series of holes and a screw connection by means of bolts. In another embodiment of the invention, provision has further been made that the mattress base has a frame of which the longitudinal girders and transverse girders are designed in such a way that their length is adjustable. In this way it is also possible to fit the mattress base within a given range, to the dimensions of an existing bed box frame.

According to another embodiment of the invention the longitudinal and transverse girders are designed as tubular profiles and are securely connected to one another by means of telescopic insertable and detachable connecting pieces. The adjustment in length of both the transverse girders and the longitudinal girders is preferably done by means of corner forming angle pieces which are designed in such a way that they can be inserted in a telescopic like way into each end of the transverse girder and of the pertinent longitudinal girder and can be attached to the bars. The connection can also be made again by means of an appropriate series of holes at the respective ends of the girders and in the ends to be inserted of the angle pieces and by insertable bolts.

According to another embodiment of the invention the end parts are designed to be adjustable with respect to width, especially with respect to the distance between the legs. This arrangement has the advantage that the end parts can be adapted exactly to the width of the bed box frames so that the end parts with a separately installed conversion set are supported on the side of the bed box frame and thus provide the necessary securing of the conversion set against lateral displacement.

According to another embodiment of the invention, the frame of the mattress base is provided with a slat platform which is connected to the frame by means of holding devices. From an orthopedic point of view a slat platform is not only an ideal support for a mattress, but also for a bed of the type according to the invention, it also has the advantage that the surface formed by the frame of the mattress base is completely clear below the slat platform so that the required free space is available for the downward tilting movement.

According to another embodiment of the invention, a pivot is installed in the standing parts to constitute a tilting bearing whenever a pivot pin attached to the frame is supported. The arrangement of a pivot, especially for a bed of the type acccording to the invention, which is produced by a later installed component, has the advantage that sagging, caused by inaccuracies during installation or also alignment errors due to unevenness of the floor as well as deformations of the mattress base under load, is corrected so that a perfect tilting movement is always possible.

BRIEF DESCRIPTION OF THE DRAWINGS

FIG. 6 is a partial view in longitudinal direction of an embodiment with holding elements holding the mattress;

FIG. 7 is a schematic view of a tilting bearing of the mattress base above height adjustable legs.

DESCRIPTION OF THE PREFERRED EMBODIMENTS

As an example, there is described, a so-called conversion set which makes it possible to convert an existing bed into a bed for snorers, which is especially desirable in the case of valuable furniture. Irrespective of the individual type of design, the bed section is described in the following as bed box frame 1. With a view to a clearer representation, the bed box frame 1 is shown in dotted lines.

The conversion is carried out in such a manner that the existing mattress base, e.g. a spring frame, is removed from the bed and the conversion set is then installed in the bed box frame. The conversion set is designed in such a way that it represents a self-contained, self-supporting structural unit. Besides the installation and the adaptation to the dimensions of the bed box frame 1, described in detail hereinafter, no additional installation measures are required such as e.g. the attachment of parts of the conversion set to the bed box frame 1.

Figure 2:
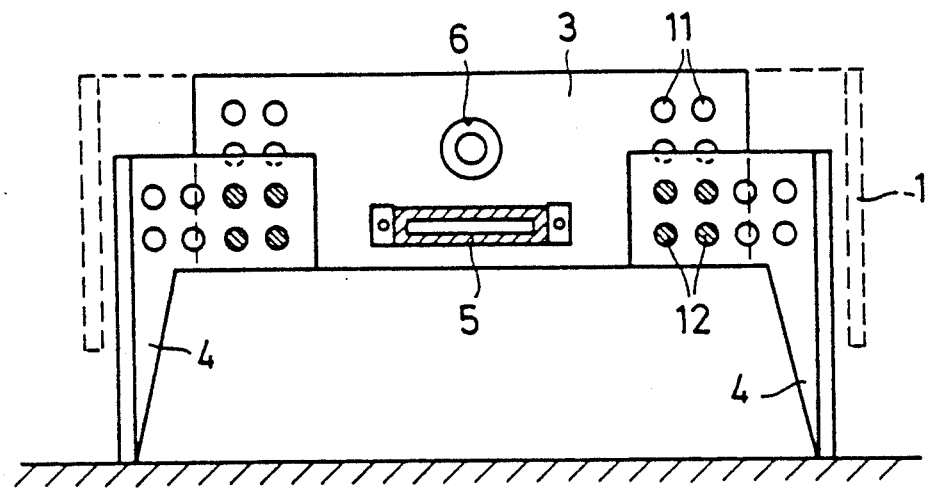
FIG. 2 is a section taken along line II—II of FIG. 1 through an end thereof without representation of the base.
Figure 3:
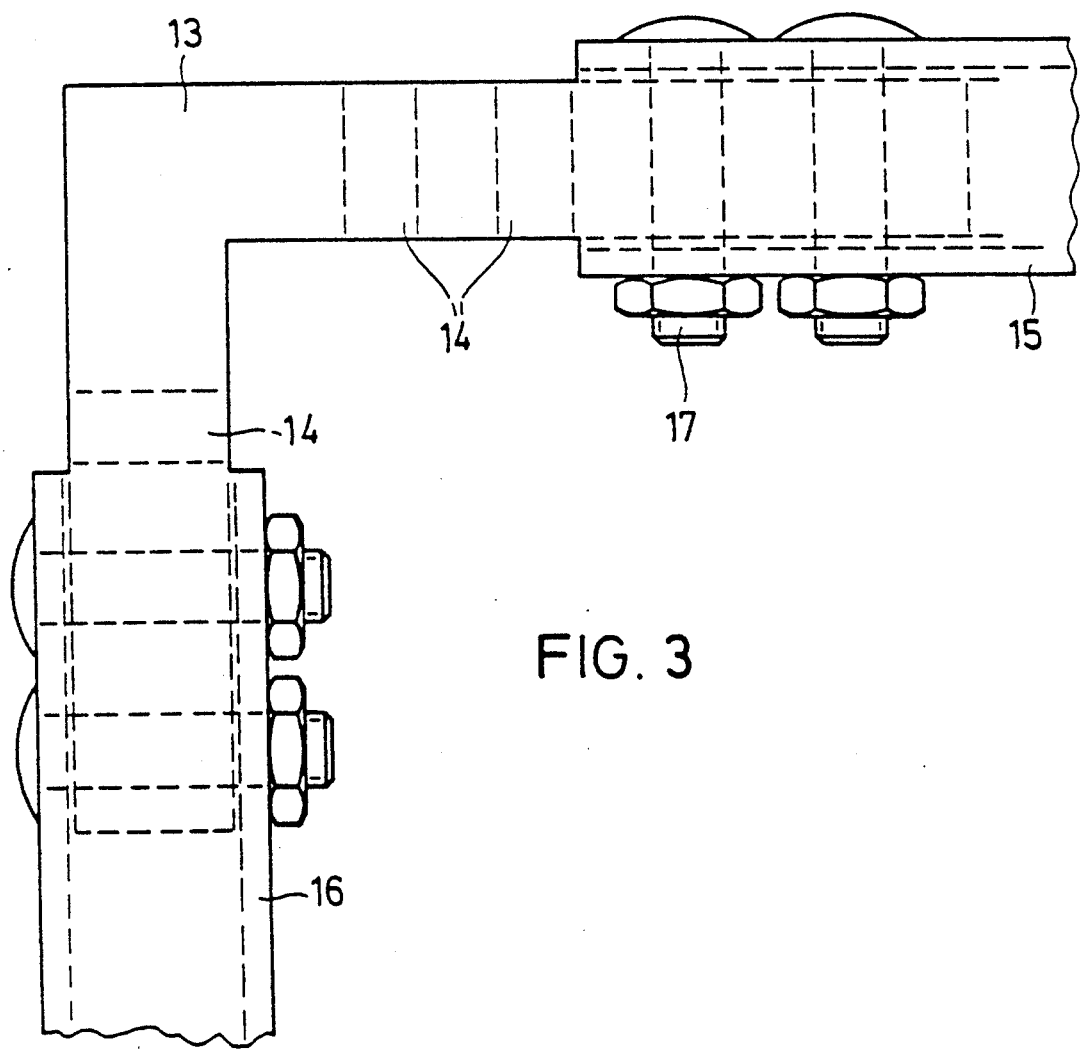
FIG. 3 illustrates on a large scale the corner of an embodiment of a mattress base which can be adjusted in length and in width.

The conversion set is essentialy made up of two end parts 2 and 3, each of which are provided with legs 4 (FIG. 2). The two end parts 2 and 3 are securely connected to one another by means of a longitudinal bar 5 which runs below the longitudinal central axis. On each of the two end parts 2 and 3 tilting bearings 6 are installed which are designed as pivots which carry a pivot pin 7 of a mattress base 8 designed as a frame. The pivot pins 7 are also in the longitudinal central axis of the mattress base 8 so that the latter can be tilted to both sides. Instead of mounting it by means of pivot pins 7, the mattress base 8 can be supported at its ends by means of two toggle joints of which the other end in each case is hinged to the end parts 2 and 3 respectively close to the floor. The toggle joints at each end are set at an angle to each other and form in each case a four-bar-chain as is indicated schematically in FIG. 7. The slope of the toggle joint 32 with respect to the horizontal and the distance of the joints 33, 34 and 35, 36 respectively to one another determines the relation of the pivot distance of the joint and the slope of the mattress base.

The mattress base 8 can be tilted to both sides into a sloping position from the horizontal position by means of a tilting drive 9, e.g. an electric geared motor, which is hinged to the end part 3 via a connecting rod 10 which is e.g. in the form of a rack.

Since, apart from the various differences in mattress size, the internal dimensions of existing bed box frames are different, depending on design of the padding of the mattress base, the conversion set is designed in such a way that, by and large, it can be adjusted both in width and length as well as with regard to height. The arrangement can be such that the drive motor 9 is installed on the end part or on the bed box frame and the connecting rod 10 is hinged to the mattress base. Instead of a rack, the connecting rod can also be in the form of a threaded spindle with is provided with a corresponding spindle nut. Depending on the design of the drive, the spindle or the spindle nut can be turned and operated by means of a motor. To support the mattress base with toggle joints, the connecting rod can also act on one of the toggle joints (cf. arrow 37 in FIG. 7)

As shown in FIG. 2, the end parts 2 and 3 are wide enough to be used in the narrowest bed box frame on the market. In addition, at the end there are in each case through the end parts a plurality of holes 11 which correspond with the holes 12 in the support legs 4. In this way it is possible to adjust the height of the longitudinal central axis of the arrangment, defined by the tilting bearing 6, with respect to the floor or with respect to the existing bed box frame 1 by means of appropriate change in height of the legs 4 with respect to the end parts 2 and 3. The width between the legs 4 can also be adjusted at the same time so as to rest against the inside of the bed box frame 1 thereby enabling the inserted part to be secured in the bed box frame 1 against sideways displacements.

Figure 1:
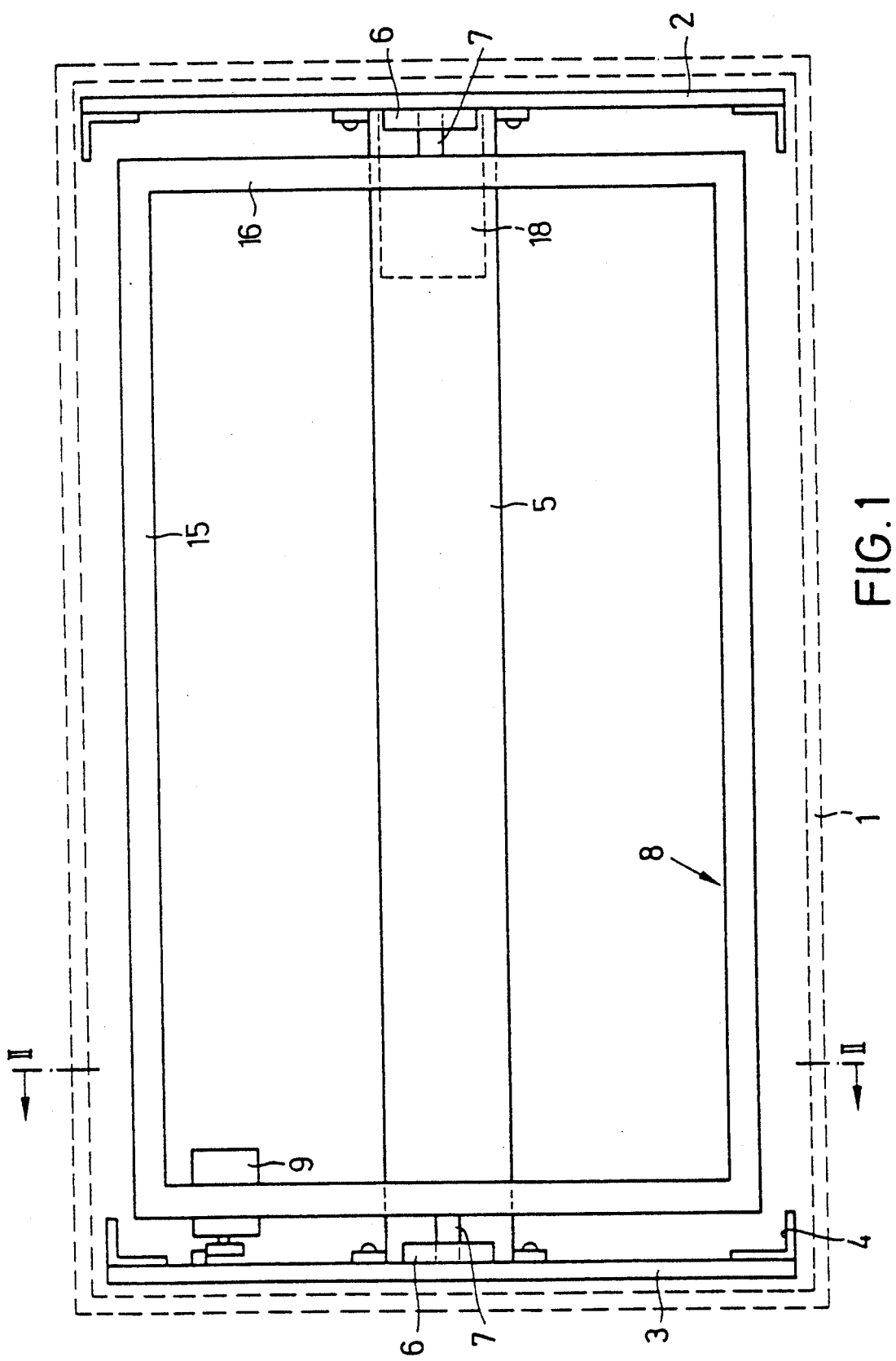
FIG. 1 is a top view of a bed box frame of a normal bed with a conversion set.

The mattress base, designed as a simple frame, in the illustrated embodiment is preferably made of tubular members. In order to also obtain the required adjustment in width and length, each corner is provided with angle pieces such as connecting pieces 13 which have cross drilled holes 14 at set intervals. These angle pieces are inserted at the ends into each of the frame forming longitudinal girders 15 and transverse girders 16 which are provided with at least two transverse drill holes. Depending on required length, the connecting piece 13 is then telescopically inserted into the longitudinal girder 15 and/or into the transverse girder 16 until the required dimension is met. The angle pieces 13 are then securely connected to the transverse girders 16 and to the longitudinal girders 15, e.g. by means of screw bolts 17. The longitudinal bar 5 is in a similar way provided with a telescopic-like connecting piece 18 which is movable with respect to the bar as is schematically shown in FIG. 1.

Figure 4:
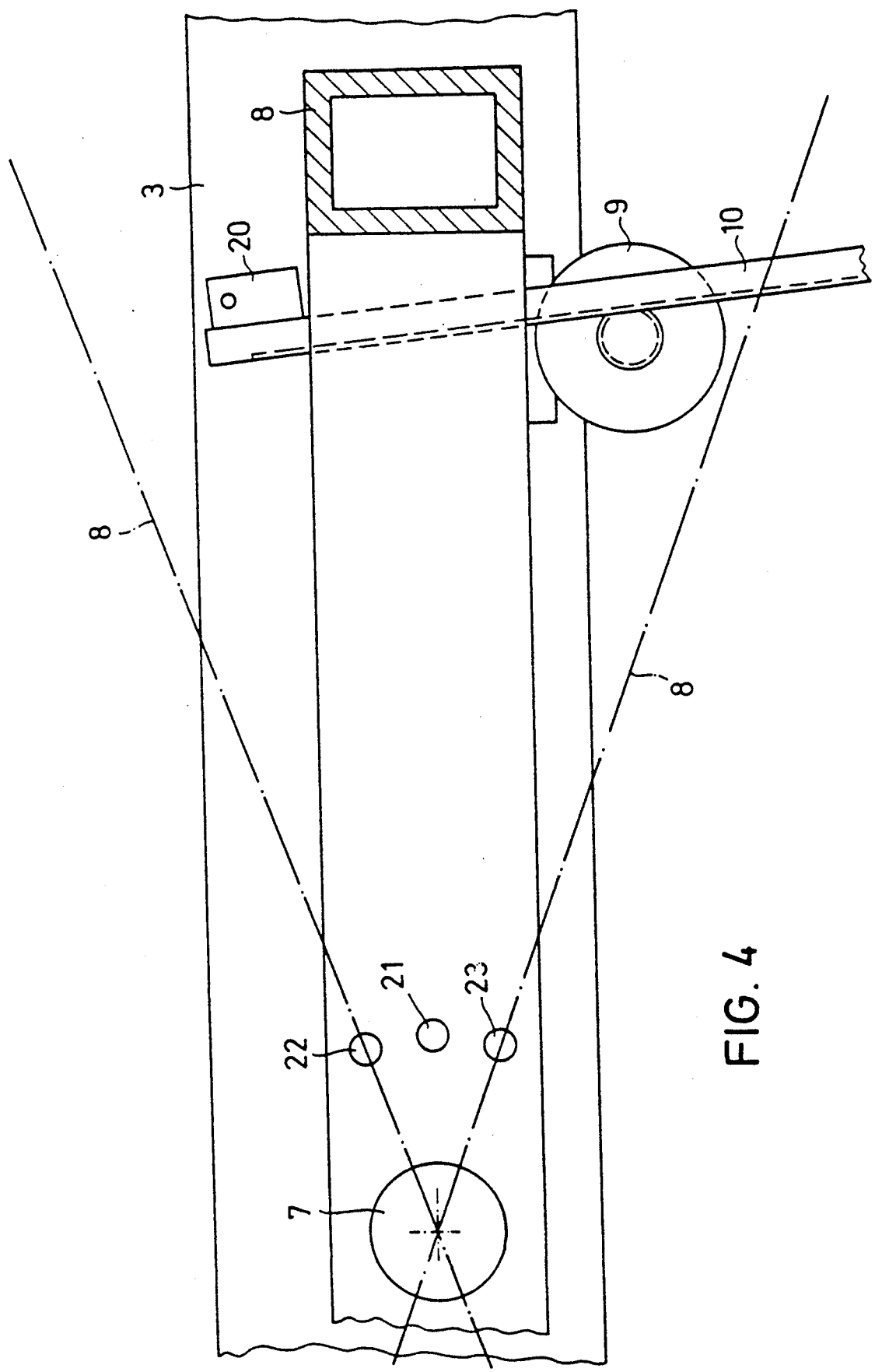
FIG. 4 is a front view of the mattress base with a tilting drive.

The arrangement and the operation of the tilting drive is further schematically illustrated in FIG. 4. In the illustrated embodiment, the tilting drive is formed of an electric geared motor 9 of which the drive shaft has a pinion 19 which interacts with teeth of the connection rod 10, constituting a rack. The geared motor is suitably installed on the underside of the mattress base 8 in order to be able to achieve the best possible utilization of the space of the existing bed box frame. The connecting rod 10 is appropriately hinged to the designated end part 2 or 3 and is kept engaged in the usual way with the pinion 19 by means of an appropriate cage on the geared motor 9. FIG. 4 shows the arrangement in the horizontal position. Depending on the direction of rotation of the geared motor 9, the mattress base 8 can now be tilted, as the case may be, upwards or downwards over an angle of between 10° and 25° with respect to the horizontal.

The joint of the connecting rod 10 to the end part 2 or 3 is provided with a load sensitive reversing switch 20 which is designed in such a way that for the application of a load on connecting rod 10 by a clockwise load moment, the rotation of the geared motor 9 is directed so that when switched on, the mattress base is tilted up counterclockwise. For an application of load on the connecting rod 10 by a load moment which acts counterclockwise, the rotation is directed by the reversing switch in such a way that a tilting of the mattress base takes place in a clockwise direction.

Further, the electric control also has limit switches which in each case when actuated, switch the geared motor off when the respective sloping position has been reached, but also when the mattress base is tilted back from the sloping position into the horizontal position. For this, three limit switches are provided which suitably are designed as non-contact limit switches. Compared to usual limit switches, these have the advantage that no maintenance is required and that thus breakdowns due to dust accumulation which is inevitable in a bedroom, are excluded.

It is, however, also possible to install appropriately enclosed limit switches. In FIG. 4 three limit switches 21, 22 and 23 are illustrated. In addition, part of the control element is installed in each case on an end part and the appropriate control element is installed on the mattress base. Since these are limit switches of usual design, they are only indicated schematically.

Figure 5:
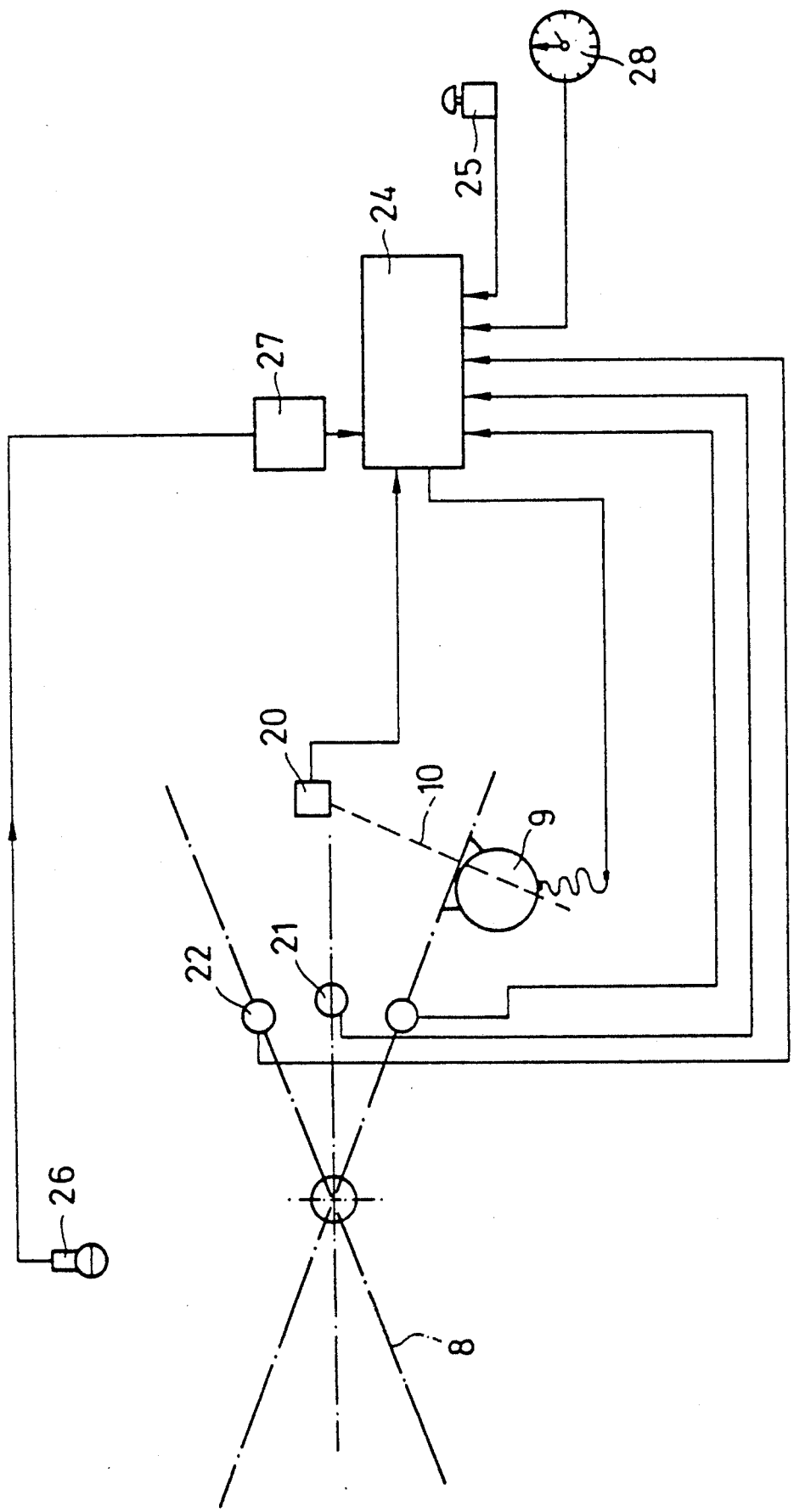
FIG. 5 is a schematic representation of an electric operating circuit.

The relation of the individual switch elements within the framework of a control is shown in FIG. 5. The three limit switches 21, 22 and 23 are first connected to an appropriately designed electric control 24 in such a way that in each case they turn off the motor when the position defined by the limit switch is reached. However, at the same time a related switch in the control is actuated as usual which permits a restart of the motor in the opposite direction.

The load sensitive switch 20 disposed on the joint of the connecting rod 10 is also connected to the control 24 so that depending on the load moment which is set by the load of the mattress base and which can change as a function of the actual position of the sleeping person, a rotation of the motor 9 opposed to the direction of the load moment takes place as soon as the motor is switched on.

The motor can be started by means of a switch 25, preferably a touch switch. In addition, in the embodiment illustrated, an electro-acoustic sensor 26 is also provided, e.g. in the form of a small microphone, which is connected in a measuring circuit 27, whose signal output is connected to control 24. The measuring circuit 27 can be designed in such a way that it transmits a control signal if, by means of the electro-acoustic sensor, a sound is detected which exceeds a given sound level. However, it is useful to design the measuring circuit in such a way that the control signal is only sent if sounds of a certain frequency and/or a given sound level are detected by the electro-acoustic sensor 26. Since snoring sounds have a very low frequency, it would thus be possible to filter this frequency range so as to prevent other sounds from triggering a control signal.

By means of a mechanical or electrical short-interval time switch 28 which also is connected via an appropriate circuit to the control 24, after a certain period of e.g. 5 to 10 minutes, the mattress base again may be tilted back from the sloping position to the horizontal position so that the sleeping person who now lies on his side, can continue to sleep undisturbed. This is of importnace, beacuse when the mattress base is kept in the sloping position for a longer period, due to the unusual position of the body and the tendency of the relaxed body lying on the mattress to roll "downwards", the sleep is interrupted, or at least, however, the deep sleep is reduced for a short time due to the movements of the muscles.

To connect the limit switches to the mattress base, they can also be integrated in the drive mechanism. The actual sloping position can also be adjusted by the setting of the connecting rod or rack on the drive motor.

As the partial view according to FIG. 6 shows, fixed comblike arranged holding elements 30, according to an embodiment, are attached to both long edges of the slat platform which forms the mattress base. The individual holding elements 30 protrude from below into the gap between each pair of slats 31 and, with the mattress base in the horizontal position, their upper ends reach preferably just below the carrying surface of the slat platform.

If the mattress base 8 is tilted, as is shown in dotted lines in FIG. 6, the edge of the supported mattress is kept at the original height by the holding elements 30 so that the mattress at the edge is deformed into a slight trough. The edge is then slightly bent up relative to the resting surface of the mattress so that the body is perfectly supported in the side position. This prevents the sleeping person, in the tilted position, from having the feeling that he might fall out of bed.

From the representation according to FIG. 6, it can be seen that the movement can also be reversed. In particular for a slat platform, the holding elements 30 make it possible to put the slat platform as usual in the bed box frame and to connect the holding elements with the drive so that when the control is actuated, the holding elements lift up the side of the mattress. For soft mattresses an appropriately rigid base has to be provided to bring a sufficiently wide area of the mattress into the sloping position which brings about the change in body position. This base is suitably hinged to or hinged close to the other long side. This base can also be formed by slats of the slat platform. The individual slats are alternately hinged to the one and to the other longitudinal girder of the frame. The other end is then supported in each case at the other long side by a holding element which can be raised and lowered. In this case the holding elements do not reach into the gap. To the holding elements 30 on each long side a drive is attached in each case which can e.g. be a connecting rod drive of the earlier mentioned design. By means of appropriate load sensitive sensors provided in the control, care must also be taken that the "right" side tilts up, thus the side on which the higher load is.

For other mattress base designs, appropriate recesses must be provided which make the passage of the holding elements possible. The arrangement of the holding elements must be designed in such a way that the tilting freedom of the mattress base is not restricted, and that the mattress is held securely at the edge.

In order to avoid injuries, a downwardly extending, encircling protective skirt 38 is attached to each of the upwards tiltable parts of the mattress base 8. When the edge of the mattress base is tilted above the edge 39 of the bed box frame 1, the formation of a gap is avoided in which one could unintentionally be caught.

For a tilting arrangement of the mattress base by means of pivot pins as shown in FIG. 1, the protective skirt 38 can be made of a rigid material, e.g. of plastic.

For a tilting arrangement by means of toggle joints, rigid shaped parts can only be installed at the edges of the ends since the tilting operation also includes a horizontally displaced component. Therefore, at the long sides protective skirts of a flexible material must be provided, e.g. a roller-blind type textile skirt which remains sufficiently tightly stretched.

As FIG. 7 shows, the drive 9, e.g. in the form of vertically oriented connecting rods, can be attached permanently in each case to bars 32 with which the holding elements 30 are connected. The slats 31 of the slat platform are alternately supported on these so that in each case, one half of the slats can be tilted up to the right and the other half to the left, depending on the control by the control. The frame 8 lies securely in the bed box frame 1.

Instead of the individual slats, the frame altogether can be tilted up either to the right or to the left. Here it is also possible to design the drives using their connecting rods at the same time as legs for the frames. However, the bars 32 can also be moved up and down by means of a tilting drive.

It will be understood that the above description of the present invention is susceptible to various modifications, changes and adaptions, and the same are intended to be comprehended within the meaning and range of equivalents of the appended claims.

What is claimed is:

1. A bed for preventing snoring, comprising:
   (a) a support;
   (b) a mattress base having a length and an essentially planar resting surface;
   (c) means for tiltably securing said matress base to said support so as to provide for tilting motions of said matress base about a longitudinal pivotal axis thereof;
   (d) drive means for imparting a tilting motion to said mattress base out of and into a horizontal position;
   (e) a load-sensitive switch means operatively connected with said mattress base and said drive means for tilting said mattress base out of the horizontal position in a direction opposite to a torque imparted by a load to said mattress base and
   (f) limit switch means operatively connected to said drive means and cooperating with said mattress base for deenergizing said drive means when said mattress base attains a predetermined tilted position during tilting motion from the horizontal position or when said mattress base attains the horizontal position during tilting motion from a tilted position.

2. A bed as defined in claim 1, wherein said mattress base has a central longitudinal axis; said longitudinal pivotal axis coinciding with said central longitudinal axis.

3. A bed as defined in claim 1, wherein said limit switch means comprises a plurality of non-contact limit switches.

4. A bed as defined in claim 1, wherein said drive means comprises an electric motor.

5. A bed as defined in claim 4, further comprising a connection rod coupled to said electric motor and said mattress base for tilting said mattress base by said electric motor through said connecting rod; further wherein said connection rod is coupled to said load-sensitive switch means.

6. A bed as defined in claim 5, wherein said connecting rod is coupled to said load-sensitive switch means.

7. A bed as defined in claim 1, further comprising a short-interval time switch means operatively connected to said drive means for energizing said drive means to return said mattress base into the horizontal position from the tilted position after a predetermined delay.

8. A bed as defined in claim 7, further comprising an electro-acoustic sensor operatively connected to said drive means for energizing said drive means in response to snoring sounds.

9. A bed as defined in claim 1, further comprising holding elements secured to said support along opposite longitudinal sides of said mattress base and being arranged for engaging edge zones of a mattress supported on said mattress base.

10. A bed as defined in claim 9, wherein said mattress base comprises a slat platform formed of a plurality of spaces slats oriented perpendicularly to the longitudinal pivotal axis; said holding elements projecting from below into gaps defined between adjoining slats; each holding element having an upper end being essentially coplanar with said slat platform in the horizontal position of said mattress base.

11. A bed as defined in claim 10, wherein said mattress base has a central longitudinal axis; further wherein said means for tiltably securing said mattress base to said support comprises a pivot pin defining said longitudinal pivotal axis; said longitudinal pivotal axis extending parallel to and spaced from said central longitudinal axis.

12. A bed as defined in claim 1, wherein said support comprises a box frame; further comprising a protective skirt secured to a longitudinal edge of said mattress base and extending downwardly into said box frame for providing a shield below said longitudinal edge when said longitudinal edge is positioned above a level of said box frame in said tilted position of said mattress base.

13. A bed for preventing snoring, comprising
(a) a support;
(b) a mattress base having a length, a longitudinal axis and an essentially planar resting surface; said mattress base comprising a slat platform formed of a plurality of spaced slats oriented perpendicularly to the longitudinal axis;
(c) means for tiltably securing said mattress base to said support so as to provide for tilting motions of said mattress base about a longitudinal pivotal axis thereof;
(d) drive means for imparting a tilting motion of said mattress base out of and into a horizontal position;
(e) limit switch means operatively connected to said drive emans and cooperating with said mattress base for deenergizing said drive means when said mattress base attains a predetermined tilted position during tilting motion from the horizontal position or when said mattress base attains the horizontal postion during tilting motion from a tilted position; and
(f) holding elements secured to said support along opposite longitudinal sides of said mattress base and being arranged for engaging edge zones of a mattress supported on said mattress base; said holding elements projecting from below into gaps defined between adjoining slats; each holding element having an upper end being essentially coplanar with said slat platform in the horizontal position of said mattress base.

* * * * *